United States Patent [19]

Aoki et al.

[11] Patent Number: 5,098,829
[45] Date of Patent: Mar. 24, 1992

[54] ANTI-THROMBIN-BINDING SUBSTANCE MONOCLONAL ANTIBODIES, HYBRIDOMAS PRODUCING SAME, AS WELL AS PURIFICATION PROCESS AND ASSAY OF THROMBIN-BINDING SUBSTANCE MAKING USE OF SAID MONOCLONAL ANTIBODIES

[75] Inventors: Nobuo Aoki, Tokyo; Takao Nagoya, Tsuchiura; Shigeru Kimura, Higashiyamato, all of Japan

[73] Assignee: Kowa Co., Ltd., Nagoya, Japan

[21] Appl. No.: 560,275

[22] Filed: Jul. 30, 1990

Related U.S. Application Data

[63] Continuation of Ser. No. 224,769, Jul. 27, 1988, abandoned.

[30] Foreign Application Priority Data

Aug. 13, 1987 [JP] Japan ................................ 62-202517

[51] Int. Cl.⁵ ..................... G01N 33/577; C12N 5/12; C07K 15/28; C07K 3/20
[52] U.S. Cl. .............................. 435/7.21; 435/240.21; 530/413; 530/388.25
[58] Field of Search .................. 435/7.1, 7.2, 7.21, 435/172.2, 240.27; 436/501, 536, 543, 548, 69, 811; 530/380, 381, 382, 387, 808, 809, 413; 935/95, 103, 106, 110

[56] References Cited

U.S. PATENT DOCUMENTS 4,775,624 10/1988 Bang et al. ........................ 436/226

OTHER PUBLICATIONS

Sevier, E. D. et al., Clin. Chem., vol. 27/11, 1981, pp. 1797–1806.
Maruyama, I. et al., J. Biol. Chem., vol. 260 (29), Dec. 15, 1985, pp. 15432–15438.

Primary Examiner—Esther L. Kepplinger
Assistant Examiner—Susan L. Futrovsky
Attorney, Agent, or Firm—Oblon, Spivak, McClelland, Maier & Neustadt

[57] ABSTRACT

The present invention provides a monoclonal antibody specific to a thrombin-binding substance (TM), hybridomas producing the monoclonal antibody, a purification process of TM featuring the use of the monoclonal antibody as an immunoadsorbent, as well as an immunoassay of TM featuring the use of the monoclonal antibody.

4 Claims, 4 Drawing Sheets

ANTI-THROMBIN-BINDING SUBSTANCE MONOCLONAL ANTIBODIES, HYBRIDOMAS PRODUCING SAME, AS WELL AS PURIFICATION PROCESS AND ASSAY OF THROMBIN-BINDING SUBSTANCE MAKING USE OF SAID MONOCLONAL ANTIBODIES

This application is a continuation of application Ser. No. 224,769, filed on July 27, 1988, now abandoned.

BACKGROUND OF THE INVENTION i) Field of the Invention

This invention relates to monoclonal antibodies capable of specifically interacting with a human-derived thrombin-binding substance and also to their utilization.

ii) Description of the Related Art

The cell fusion technology has been developed rapidly since the report of Kohler and Milstein [Nature, 495–497 (1975)]. It has been known that a hybridoma obtained by fusing mammalian spleen cells and myeloma cells produces various antibodies depending on the characteristics of the spleen cells employed. It has also been attempted to form a hybridoma, which produces a monoclonal antibody against various biological substances such as proteins and hormones, by effecting cloning based on the characteristics of the hybridoma and also to produce the monoclonal antibody [E. Dale Servier et al., Clinical Chemistry, 27(11), 1779–1806 (1981)].

In the meantime, the present applicant previously succeeded in isolating from the human placenta a thrombin-binding substance (hereinafter called "TM"), which binds thrombin and specifically enhances activation of Protein C, and purifying same (Japanese Patent Application Laid-Open No. 199819/1985). TM has the following properties and is hence useful as a medicine.

(1) Molecular weight:
  $88,000 \pm 10,000$ in reduced state; and
  $71,000 \pm 10,000$ in non-reduced state.
(2) Isoelectric point:
  pH $4.2 \pm 0.5$.
(3) Affinity:
  Strong affinity to thrombin.
(4) Activities:
  (a) Capable of binding thrombin and activating Protein C.
  (b) Capable of prolonging the clotting time.
(5) Stability:
  Stable in a pH range of 2–10.
  Stable against treatment by a denaturing agent (sodium dodecylsulfate or urea) or pepsin.

Further, the human-derived TM has thereafter been reported in the following articles, patent publications, etc.

Derived from the placenta:
  J. Biol. Chem., 259, 12246–12251 (1984).
  Thrombosis Research, 37, 353–364 (1985).
  EP182929A.
Derived from the lung:
  WO 87/0050.
Derived from plasma or urine:
  J. Clin. Invest., 76, 2178–2181 (1985).
Derived from hemangioendothelial cells or pulmonary carcinoma cells:
  J. Biol. Chem., 260, 15432–15438 (1985).

TM is however contained only in a trace amount in the placenta, and no sufficient specific binding is established with TM in various chromatographic techniques which are employed routinely. It is hence difficult to obtain TM in a highly pure form. Moreover, such conventional procedures require many steps and are unable to achieve any satisfactory recovery rate.

It has therefore been desired to develop a specific purification process for obtaining high-purity TM easily in a high yield.

It has also been desired to develop a high-sensitivity assay for TM as a means for the elucidation of the mechanism of the action of TM and also for the measurement of its blood level.

I. Maruyama, et al. have already prepared an anti-TM monoclonal antibody by using TM derived from the human placenta and investigated whether the antibody would inhibit the activation of Protein C caused as a result of binding of thrombin by TM derived from hemangioendothelial cells or pulmonary carcinoma cells [J. Biol. Chem., 260, 15432–15438 (1985)]. However, the discussion of this article only shows the property of the monoclonal antibody that it can recognize a thrombin-binding site of TM. It discloses nothing about other biological and physicochemical properties of the monoclonal antibody.

SUMMARY OF THE INVENTION

The present inventors have carried out an extensive investigation with a view toward obtaining more useful anti-TM monoclonal antibody. As a result, it has been found that a novel monoclonal antibody having unique properties can be obtained by testing characteristic properties in respect to monoclonal antibodies produced by hybridomas obtained by fusing antibody-producing cells of an animal, which has been immunized with TM by a conventional method, with myeloma cells, namely, by testing whether they can recognize a thrombin-binding site of TM, whether they can recognize a structural change of TM caused by calcium ions and whether they can recognize a variation in molecular weight of TM due to its treatment with a protease, and screening the novel monoclonal antibody. It has also been found that the use of the monoclonal antibody permits high-level purification and immunoassay of TM, thereby leading to completion of this invention.

In one aspect of the invention, there is thus provided a monoclonal antibody selected from a group consisting of those named "TM-A54", "TM-A59", "TM-A60", "TM-A65", "TM-A73" and "TM-A91" respectively, said antibody being capable of specifically interacting with a human-derived thrombin-binding substance which binds thrombin and specifically enhances activation of Protein C.

In another aspect of the invention, there is also provided hybridomas selected from a group consisting of those named "TM-H54", "TM-H59", "TM-H60", "TM-H65", "TM-H73" and "TM-H91" respectively, said hybridomas being obtained by fusing antibody-producing cells of an animal immunized with a human-derived thrombin-binding substance, which binds thrombin and specifically enhances activation of Protein C, with myeloma cells and being capable of specifically interacting with the thrombin-binding substance.

In a further aspect of the invention, there is also provided a process for purifying a thrombin-binding substance by immune affinity column chromatography, which comprises the use of a monoclonal antibody selected from a group consisting of those named "TM-A54", "TM-A59", "TM-A60", "TM-A65", "TM- A73" and "TM-A91" respectively and being capable of specifically interacting with a human-derived thrombin-binding substance which binds thrombin and specifically enhances activation of Protein C.

In a still further aspect of the invention, there is also provided an assay of a thrombin-binding substance, which comprises the use of a monoclonal antibody selected from a group consisting of those named "TM-A54", "TM-A59", "TM-A60", "TM-A65", "TM-A73" and "TM-A91" respectively and being capable of specifically interacting with a human-derived thrombin-binding substance which binds thrombin and specifically enhances activation of Protein C.

Hybridomas according to this invention produce a monoclonal antibody specific to TM. Since this monoclonal antibody specifically interacts not only with the above-described TM derived from the human placenta but also with TM derived from human urine, TM derived from human plasma, TM derived from the human lung and the like, the use of the monoclonal antibody allows to shorten separation and purification steps for various TMs and moreover permits the provision of the TMs of extremely high purity at a high recovery rate. On the other hand, an solid carrier with the monoclonal antibody coupled thereon can be used repeated provided it is washed. Accordingly, it can shorten the purification step and is economical. It is hence extremely useful in the industry.

Anti-TM monoclonal antibodies according to this invention can also be used for the immunoassay of TM in the treatment of abnormality and diseases in the coagulative fibrinolysis system.

BRIEF DESCRIPTION OF THE DRAWINGS

The above and other objects, features and advantages of the present invention will become apparent from the following description and the appended claims, taken in conjunction with the accompanying drawings, in which:

FIG. 1: "TM-A59" and "TM-A73" were used respectively as a coating monoclonal antibody and as a monoclonal antibody to be conjugated.

FIG. 2: "TM-A60" and "TM-A73" were used respectively as a coating monoclonal antibody and as a monoclonal antibody to be conjugated.

FIG. 3: "TM-A59" and "TM-A91" were used respectively as a coating monoclonal antibody and as a monoclonal antibody to be conjugated.

FIG. 4: "TM-A59" and "TM-A60" were used respectively as a coating monoclonal antibody and as a monoclonal antibody to be conjugated.

DETAILED DESCRIPTION OF THE INVENTION AND PREFERRED EMBODIMENTS

Figure 1:
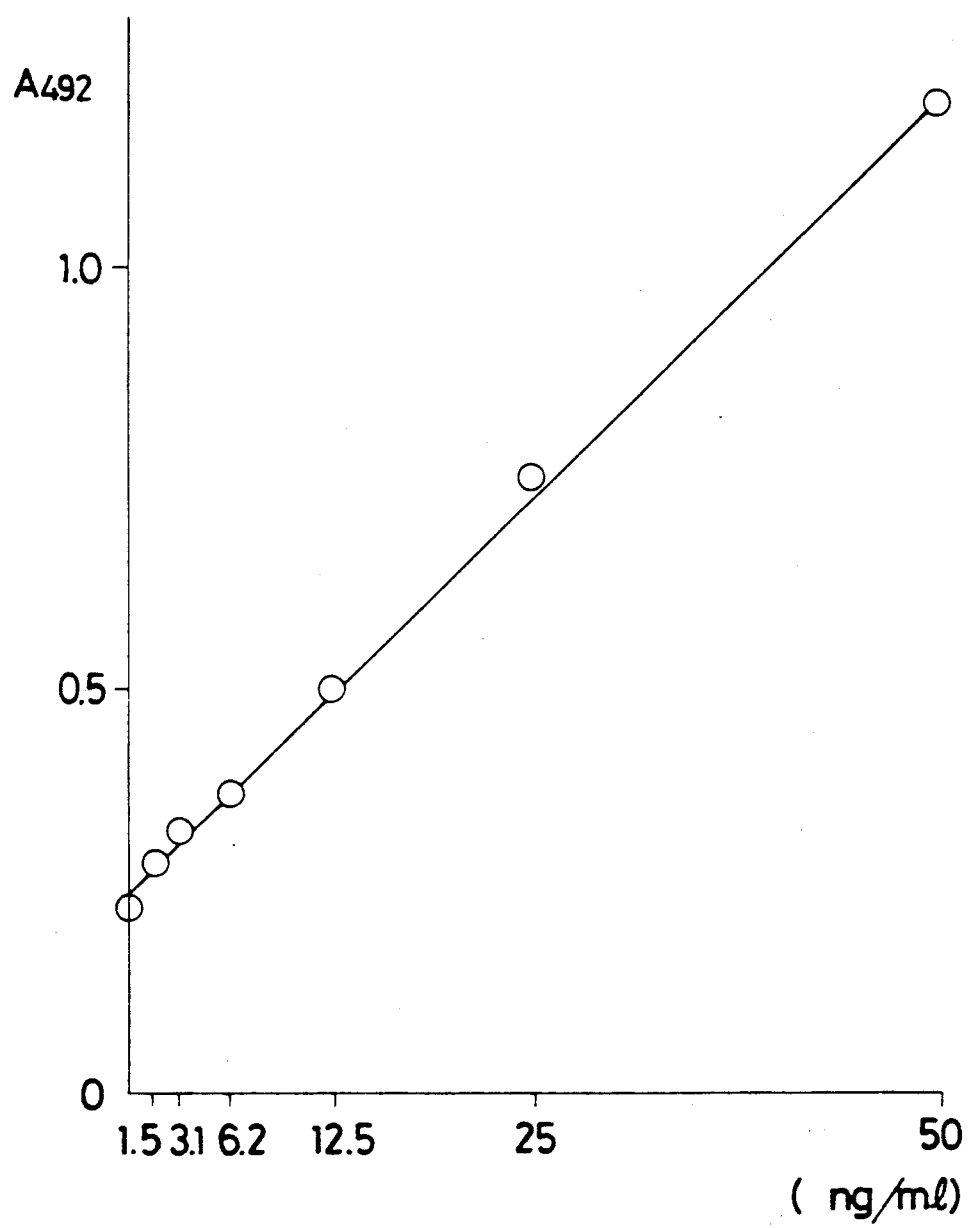
FIGS. 1, 2, 3 and 4 illustrate the absorbance (at 492 nm) as a function of the TM concentration in the assay of TM in Example 4.

The hybridomas which produce the monoclonal antibody specific to TM may be formed, for example, in the following manner. (1) Antibody-producing cells are prepared from an animal which has been immunized with TM as an antigen. (2) Myeloma cells are cultured. (3) These cells are caused to fuse together. (4) The resulting hybridomas are allowed to grow selectively. (5) Antibody-producing hybridomas are screened out from the hybridomas. (6) Using a culture medium of the antibody-producing hybridomas, it is tested whether the monoclonal antibody in the culture medium can recognize (i) a thrombin-binding site of TM, (ii) a structural change of TM caused by calcium ions and (iii) a variation in molecular weight of TM caused by its treatment with an enzyme. (7) Hybridomas producing the intended monoclonal antibody are obtained by cloning.

Each of the above steps will next be described.

(1) Preparation of antibody-producing cells:

The preparation of antibody-producing cells may be conducted in accordance with a method known commonly in the art. This may be done by immunizing an animal with TM as an antigen and then collecting antibody-producing cells from the animal. A mouse, rat, rabbit, guinea pig, sheep or the like may be mentioned by way of example as the animal. As the antibody-producing cells to be collected, may be mentioned those separated from spleens, lymph nodes, peripheral blood or the like. As an immunizing method, it is preferable to emulsify TM, for example, in Freund's complete adjuvant and where a mouse is used by way of example, to administer the resultant emulsion either subcutaneously or intraperitoneally, and to continue the administration for 1-20 months at intervals of 1-5 weeks so as to complete the immunization.

(2) Preparation of myeloma cells:

No particular limitation is imposed on myeloma cells to be used in the cell fusion. Cell strains of many mammals may be used. It is however preferable to use the cell strains of an animal which belongs to the same family as the animal used for the antibody-producing cells. It is preferable to use a cell strain having specific chemical resistance, so that unfused cells and fused cells can be separated from each other after the cell fusion by incubating both unfused and fused cells in a selective medium in which unfused myeloma cells cannot survive but hybridomas alone are allowed to grow. For example, 8-azaguanine resistant cells are favorably employed because they cannot grow in HAT medium. As specific cell strains useful in the practice of this invention, may be mentioned mouse myeloma cell strains P3-Ag8-γ, P3-X63-Ag8, P3-X63-Ag8-U1, NSI-Ag4/1, X63-Ag8.6.5.3, SP2/0-Ag14, MPC11-45.6TG1.7, FO, S194/5XXO.BU.1, etc.

(3) Cell fusion:

The cell fusion is effected usually by mixing antibody-producing cells and myeloma cells at a ratio of 10:1-1:1 in a medium such as MEM medium, PRMI1640 medium or IMDM medium. As a fusion promoter, it is preferable to use polyethylene glycol the average molecular weight of which may range from 1,000 to 6,000. Polyethylene glycol may be employed usually at a concentration of 30-50%.

(4) Selective growth of hybridomas:

Cells which have gone through the cell fusion are diluted suitably, for example, with IMDM medium containing fetal calf serum, followed by centrifugation. The resultant sediment is suspended in a selective medium (for example, HAT medium), poured in portions into a 96-well microtiter plate, and then cultured to grow hybridomas alone.

(5) Screening of antibody-producing hybridomas:

The screening of antibody-producing hybridomas may be effected by a method known per se in the art. For example, the screening may be conducted by collecting cultured media with hybridomas grown therein, reacting the antibody in the cultured medium with TM and then reacting the resultant product further with a second antibody labelled with an enzyme, fluorescent substance or light-emitting substance.

(6) (i) Recognition of a thrombin-binding site of TM:

It is only necessary to investigate the reactivity of the antigen-antibody reaction product, which has been obtained above in the procedure (5), with thrombin. Following Experiment 1 to be described subsequently, a judgement can be made depending whether TM binds thrombin to inhibit the activation of Protein C. Namely, inhibition of the activation indicates that the monoclonal antibody has recognized a thrombin-binding site of TM. On the other hand, lack of such inhibition indicates that the monoclonal antibody has not recognized the thrombin-binding site of TM.

(ii) Recognition of a structural change of TM caused by calcium ions:

It is only necessary to investigate the reactivity in the above procedure (5) by adding EDTA to the culture, in which calcium ions are contained, in accordance with Experiment 2 to be described subsequently. Namely, occurrence of the antigen-antibody reaction indicates that the structural change has not been recognized. On the other hand, lack of the reaction indicates that the structural change has been recognized.

(iii) Recognition of a variation in molecular weight of TM caused by its treatment with a protease:

It is only necessary to investigate the reactivity in the above procedure (5) after treating TM with a protease in accordance with Experiment 3 to be described subsequently. Namely, occurrence of the antigen-antibody reaction indicates that the variation in molecular weight has not been recognized. On the other hand, lack of the reaction indicates that the variation in molecular weight has been recognized.

(7) Cloning:

Cells in a culture well, which has been found to contain antibody-producing hybridomas, are subjected to cloning in accordance with the limiting-dilution method or the like, whereby a hybridoma producing the monoclonal antibody is obtained.

Following the above-described procedures, hybridomas producing the monoclonal antibody specific to TM can be obtained.

The present inventors obtained hybridomas, which have been named "TM-H54", "TM-H59", "TM-H60", "TM-H65", "TM-H73" and "TM-H91" respectively, by the procedures to be described subsequently in Examples. These hybridomas are novel cells which can each produce a monoclonal antibody specific to TM. A procedure was therefore taken to deposit these cells with Fermentation Research Institute, Agency of Industrial Science and Technology, Government of Japan [TM-H59 (FERM BP-1697), TM-H60 (FERM BP-1698), TM-H73 (FERM BP-1699), TM-H91 (FERM BP-1700)].

The following procedure may be mentioned to obtain the monoclonal antibody specific to TM from hybridomas obtained as described above. Namely, the monoclonal antibody of this invention can be obtained from a culture supernatant by culturing antibody-producing hybridomas in a suitable medium. In order to form the monoclonal antibody in a large volume, a mineral oil such as pristane (2,6,10,14-tetramethylpentadecane) is peritoneally administered to an animal of the same family as an animal used to obtain the myeloma cells and the antibody-producing hybridomas are then inoculated, whereby the antibody-producing hybridomas are allowed to grow in vivo to a large volume.

According to the above-described method, the monoclonal antibody is formed at a high concentration in both serum and ascitic fluid of the inoculated animal. The separation and purification of the monoclonal antibody may be practised in accordance with a method which is used routinely for the purification of an antibody from serum.

Although the monoclonal antibody specific to TM is obtained as described above, properties of the monoclonal antibody differ slightly depending on the kind of hybridomas used. This may be interpreted in such a way that even with the same TM, different antibody-producing cells recognize different sites.

Properties of monoclonal antibodies TM-A54, TM-A59, TM-A60, TM-A65, TM-A73 and TM-A91, which the present inventors prepared from the above-described hybridomas, will be described hereinafter. Incidentally, their molecular weights were measured by SDS-polyacrylamide gel electrophoresis, their isoelectric points were measured by isoelectric point electrophoresis (an LKB-isoelectric point electrophoretic apparatus), and their immunoglobulin subclasses by the Ouchterlony's double immunodiffusion test [a rabbit polyclonal antibody (product of Miles Laboratories Ltd.) was used].

"TM-A54"

(a) Molecular weight: $175,000 \pm 5,000$.

(b) IgG Subclass: $IgG_1$.

(c) Isoelectric point: pH 7.2-7.7.

(d) Capable of recognizing a thrombin binding-site of the TM.

(e) Capable of recognizing a structural change of the TM, which is caused by calcium ions.

(f) Incapable of recognizing a variation in molecular weight of the TM, which is caused by a protease.

TM is known to bind $Ca^{2+}$ ions. Since "TM-A54" recognizes a structural change of TM caused by $Ca^{2+}$ ions, the use of the antibody allows to distinguish TM, whose $Ca^{2+}$-binding site has been damaged for example due to a congenital hereditary disease or other disease, from normal TM and vice versa.

"TM-A59"

(a) Molecular weight: $190,000 \pm 5,000$.

(b) IgG Subclass: $IgG_1$.

(c) Isoelectric point: pH 7.1-7.6.

(d) Incapable of recognizing a thrombin binding-site of the TM.

(e) Incapable of recognizing a structural change of the TM, which is caused by calcium ions.

(f) Incapable of recognizing a variation in molecular weight of the TM, which is caused by a protease.

Since "TM-A59" is not affected at all by the change due to binding of $Ca^{2+}$ ions by TM and also reacts to TM treated with a protease such as elastase, the antibody can recognize even that having no activities as TM by a hereditary disease or the like by way of example or even that subjected to degradation due to abnormal acceleration of activities of protease in blood.

"TM-A60"

(a) Molecular weight: $180,000 \pm 8,000$.

(b) IgG Subclass: $IgG_1$.

(c) Isoelectric point: pH 7.9-9.2.

(d) Incapable of recognizing a thrombin binding-site of the TM.

(e) Incapable of recognizing a structural changes of the TM, which is caused by calcium ions.

(f) Capable of recognizing a variation in molecular weight of the TM, which is caused by a protease.

Since this antibody does not react to TM whose molecular weight has been lowered by its treatment with a protease, it can detect, for example, only high molecular TM which exists with patients of a disease accompanied by damaged endothelial cells, such as DIC or lung cancer, but does not exist with normal men.

"TM-A65"

(a) Molecular weight: 190,000±5,000.
(b) IgG Subclass: IgG$_1$.
(c) Isoelectric point: pH 7.0-7.5.
(d) Incapable of recognizing a thrombin bindingsite of the TM.
(e) Incapable of recognizing a structural change of the TM, which is caused by calcium ions.
(f) Incapable of recognizing a variation in molecular weight of the TM, which is caused by a protease.

This antibody can be used for substantially the same purposes as "TM-59".

"TM-A73"

(a) Molecular weight: 200,000±5,000.
(b) IgG Subclass: IgG$_1$.
(c) Isoelectric point: pH 7.0-7.5.
(d) Capable of recognizing a thrombin binding-site of the TM.
(e) Capable of recognizing a structural change of the TM, which is caused by calcium ions.
(f) Incapable of recognizing a variation in molecular weight of the TM, which is caused by a protease.

This antibody can be used for substantially the same purposes as "TM-54".

"TM-A91"

(a) Molecular weight: 195,000±5,000.
(b) IgG Subclass: IgG$_1$.
(c) Isoelectric point: pH 7.0-7.4.
(d) Incapable of recognizing a thrombin binding-site of the TM.
(e) Capable of recognizing a structural change of the TM, which is caused by calcium ions.
(f) Incapable of recognizing a variation in molecular weight of the TM, which is caused by a protease.

Since this antibody can recognize the structural change of TM caused by its binding of $Ca^{2+}$ ions, it can distinguish TM, whose $Ca^{2+}$-binding site has been lost for example due to a hereditary disease or by an enzyme, from normal TM and vice versa.

As described above, TM is purified by using the monoclonal antibody of this invention as an immunoadsorbent. This may be practised, for example, by coupling the monoclonal antibody of this invention with a solid carrier such as dextran gel, agarose gel or polyvinyl gel and then subjecting crude TM to chromatography on a column of the monoclonal antibody coupled carrier as an immunoadsorbent. The coupling of the solid carrier and monoclonal antibody is effected in accordance with the cyanogen bromide method or via epoxy, amino, carboxyl or formyl groups.

The crude TM is charged into the column in which the solid carrier with the monoclonal antibody coupled thereon is packed. By eluting TM adsorbed on the column, TM can be obtained in a highly pure form.

The immunoassay of TM, which makes use of the monoclonal antibodies of this invention, may be practised, for example, in the following manner. The monoclonal antibody of this invention is labelled with a labelling agent such as an enzyme, isotope or fluorescent substance. A TM-containing sample is then added to the resultant conjugate. The degree of labelling of the immunoreaction product between the TM and conjugate is thereafter measured. The ELISA method may also be used as a general method.

Having generally described the invention, a more complete understanding can be obtained by reference to certain specific examples, which are provided herein for purposes of illustration only and are not intended to be limiting unless otherwise specified.

EXAMPLES

This invention will hereinafter be described more specifically by the following Examples.

EXAMPLE 1

Formation of Hybridomas Producing Anti-TM Monoclonal Antibody (1) Preparation of immunized spleen cells:

TM (molecular weight: 71,000; 20 μg), which had been extracted from human placentae and purified, was emulsified in the Freund's complete adjuvant and administered subcutaneously to male BALB/c mice. TM (20-100 μg) was thereafter administered peritoneally to the mice with intervals of 2-4 weeks for 10 months and finally, 100 μg of TM was administered intravenously.

Three days later, spleens were taken out of the mice, disintegrated in Iscove's Modified Dulbecco's Medium (IMDM) and filtered through a 100-mesh screen, whereby isolated spleen cells passed through the screen were obtained. A hypotonic solution (155 mM ammonium chloride) was added to the thus-obtained immunized spleen cells to subject red blood cells to hemolysis. The cells were then washed three times with IMDM.

(2) Preparation of myeloma cells:

Mouse myeloma cells (P3-Ag8-γ) were cultured in IMDM which had been added with 10% of fetal calf serum (FCS). They were subcultured with intervals of 3 days. One day before scheduled fusion, the medium was replaced by a fresh medium and cells having a survival rate of at least 90% were washed three times with IMDM.

(3) Cell fusion:

The cells prepared respectively in the above procedures (1) and (2) were both counted. The spleen cells and myeloma cells were combined together at a ratio of 3:1, followed by centrifugation. The supernatant was decanted out, and after loosening and separating the resultant cell sediment, 1 ml of 50% polyethylene glycol 1,500 was added dropwise to effect fusion. After allowing the resultant mixture to stand at room temperature for 30 seconds, 1 ml of IMDM was added dropwise over 1 minute. The resultant mixture was thereafter mixed gently while adding 10 ml of IMDM dropwise over 5 minutes to a final volume of 50 ml. The thus-prepared mixture was then centrifuged at 1,000 rpm for 8 minutes.

(4) Selection of hybridomas:

The resulting sediment was suspended in IMDM which had been added with 10% of FCS. The suspension was centrifuged again and the resultant supernatant was decanted out. The resultant cells were suspended at a concentration of $3 \times 10^5$ cells/ml in HAT-containing IMDM added with 10% of FCS. The cell suspension was poured in 100-μl portions into the individual wells of a 96-well microplate. Each well was added with 50 μl of the medium every third-fourth day. The selection of the medium allowed hybridomas alone to grow.

(5) Screening of antibody-producing hybridomas:

The culture medium in each well, in which hybridomas had grown, was collected and a test was performed by enzyme immunoassay to determine if an antibody against TM had been produced there. Namely, TM was poured at a rate of 0.5 μg/100 μl/well into each well of the 96-well microplate. The microplate was left over at 4° C. for 18 hours so as to adsorb TM. Thereafter, a culture medium as a sample was poured at a rate of 100 μl/well to react at 25° C. for 2 hours. After washing the culture medium three times with a phosphate-buffered saline containing 0.05% of "Tween 20" (trade name), horse radish peroxidase (HRP) conjugated goat anti-mouse IgG was added at a rate of 100 μl/well and two hours later, the culture was washed three times with PBS-Tween. Each well was then added with a 0.1M citric acid-sodium hydroxide buffer (pH 4.0) containing 0.001% of hydrogen peroxide and 0.4 mg/ml of orthophenylene diamine. After allowing them to react at 25° C. for 30 minutes, 4.5M sulfuric acid was added at a rate of 50 μl/well and the absorbance was measured at a wavelength of 492 nm.

(6) Selection of hybridomas producing the intended monoclonal antibody:

Using the culture medium of each stained well, the following Experiment 1, 2 and 3 were conducted.

EXPERIMENT 1

Inhibitory Effects for the Activating Ability of Protein C

TM derived from human placentae was dissolved at a concentration of 200 μg/ml in 0.02M tris-HCl buffer (pH 7.6) which contained 0.1M of sodium chloride and 0.1% of Lubrol PX. Combined were 10 μl of the resultant solution and 10 μl of each hybridoma cultured medium. The resultant mixture was incubated at 37° C. for 1 hour.

The above reaction mixture was added with 30 μl of 0.02M tris-HCl buffer of human Protein C (pH 7.5), which contained 0.15M of sodium chloride and 5 mM of calcium chloride, and also with 50 μl of the same buffer of bovine-derived thrombin (5 U/ml). After incubating the resulting mixture at 37° C. for 30 minutes, 100 μl of 0.05M tris-HCl buffer of human antithrombin III (2 U/ml), which contained 0.15M of sodium chloride, was added, followed by incubation at 37° C. for 10 minutes. Next, 200 μl of a solution of MCA substrate dissolved (0.2 mM) in the same buffer as that employed above was added, followed by incubation at 37° C. for 10 minutes. The thus-prepared mixture was then added with 600 μl of 20% acetic acid and the concentration of the resulting AMC was measured by a fluorometer.

Commercially-available normal mouse IgG was used as a control. Each antibody whose measurement value was different from the measurement value of the control was determined to have inhibitory effects (in other words, to recognize a thrombin-binding site).

EXPERIMENT 2

Effects of $Ca^{2+}$

A 96-well microplate was coated with TM (1000-fold dilution) derived from human placentae. A 1:1 mixture of each hybridoma cultured medium and PBS-Tween containing 10 mM of EDTA was added in 100-μl portions to the individual wells of the microtiter plate, followed by incubation at 25° C. for 2 hours.

After washing each well of the microtiter plate with PBS-Tween, a PBS-Tween solution of goat-anti-mouse IgG labelled with HRP was added, followed by incubation at 25° C. for 2 hours. After washing each well with PBS-Tween, a substrate solution (0.1M citrate buffer containing 0.4 mg/ml of orthophenylenediamine and 0.01% of hydrogen peroxide; pH 5.0) was added in 100-μl portions to the individual wells of the microplate, followed by incubation at 25° C. for 30 minutes. After 4.5M sulfuric acid was added in 50-μl portions to the individual wells of the microplate to terminate the respective reactions, absorbances at 492 nm were then measured separately. Those having an absorbance different from that determined in the procedure (5) of Example 1 were regarded as being affected by calcium ions (namely, being capable of recognizing a structural change caused by calcium ions).

EXPERIMENT 3

Reaction with Protease-Treated TM

Reacted at 37° C. for 30 minutes were 10 μl of a tris-HCl buffered saline (hereinafter referred to as "TBS") containing 1 mg/ml of TM derived from the human placenta and 10 μl of a TBS solution containing 100 μg/ml of trypsin ("Type XIII", trade name; product of Sigma Chemical Company) or 10 μl of a TBS solution containing 2 mg/ml of elastase (derived from porcine; product of Sigma Chemical Company). The reaction mixture was subjected to SDS-PAGE (concentration of acrylamide: 10%) by the Laemmuli's system method, followed by Western blotting. A nitrocellulose membrane and a solution, which had been obtained by diluting each hybridoma cultured medium tenfold in a tris-buffered saline containing 0.05% of Tween 20 (pH 7.6; hereinafter referred to as "TBS-Tween"), were incubated at 25° C. for 3 hours. After washing the membrane with TBS-Tween, a TBS-Tween solution of HRP-conjugated goat anti-mouse IgG was added, followed by an incubation at 25° C. for 3 hours. The reaction mixture was washed with TBS-Tween, and was then stained in 10 ml of methanol containing 30 mg of 4-chloro-1-naphthol and 50 ml of a TBS solution containing 30 μl of 30% hydrogen peroxide. Each stained membrane was regarded as having reacted with the enzyme-treated TM (namely, as being incapable of recognizing a variation in molecular weight).

From the results of the above experiments, the following 6 types of hybridomas were selected.

"TM-H54"
Experiment 1: Equipped with inhibitory effects.
Experiment 2: Affected.
Experiment 3: Reactive.
"TM-H59" (FERM BP-1697)
Experiment 1: Not equipped with inhibitory effects.
Experiment 2: Not affected.
Experiment 3: Reactive. "TM-H60" (FERM BP-1698)
Experiment 1: Not equipped with inhibitory effects.
Experiment 2: Not affected.
Experiment 3: Not reactive.
"TM-H65"
Experiment 1: Not equipped with inhibitory effects.
Experiment 2: Not affected.
Experiment 3: Reactive.
"TM-H73" (FERM BP-1699)
Experiment 1: Equipped with inhibitory effects.
Experiment 2: Affected.
Experiment 3: Reactive.
"TM-H91" (FERM BP-1700)
Experiment 1: Not equipped with inhibitory effects.

Experiment 2: Affected.
Experiment 3: Reactive.

(7) Cloning of hybridomas producing a monoclonal antibody specific to TM:

Abdominal cells collected by injecting IMDM into the abdominal cavity of a mouse were used as feeder cells. The abdominal cells suspended at $1 \times 10^5$ cells/ml in 10% FCS-added IMDM were poured in 50-$\mu$l portions into the individual wells of a 96-well microtiter plate. On the following day, antibody-producing hybridomas were prepared at a concentration of 5 cells/ml and poured in 100-$\mu$l portions into the individual wells. Every third day, a fresh supply of the same culture medium was added or the culture medium was replaced by a fresh supply, of the same medium, and culture supernatants were successively sampled out from wells in which hybridomas had grown. Confirmation of the production of the antibody was conducted by the same method as that described above. The cultures of positive wells were cloned again to obtain hybridomas producing an anti-TM monoclonal antibody.

EXAMPLE 2

Preparation of Anti-TM Monoclonal Antibody

Seven-weeks-old BALB/c mice were intraperitoneally administered with 0.5 ml of pristane (product of Aldrich Chemical Co., Inc.). About one week later, the mice were intraperitoneally inoculated with the above-obtained hybridomas at a rate of $1 \times 10^6$ cells/mouse. About 10 days later, ascitic fluid was collected from the mice. The fluid was centrifuged at 3,000 rpm for 10 minutes to collect a supernatant.

To 4.8 ml of the supernatant, an equal amount of 1.5M glycine buffer (pH 8.9) containing 3M of sodium chloride was added. The resultant mixture was subjected to chromatography on a column packed with 5 ml of "Protein A Sepharose CL-4B" (trade name) which had been equilibrated with the same buffer. After washing the column thoroughly with the same buffer, the column was eluted with 0.1M citrate buffer (pH 4.0). The eluate was collected in 3-ml portions in test tubes which contained 1 ml of 1M tris-HCl buffer (pH 8.0). $A_{280}$ was measured to collect protein fractions. After dializing the protein fractions against water, they were lyophilized to obtain an anti-TM monoclonal antibody.

Thirty milligrams of "TM-A54" were obtained from the use of "TM-H54" as hybridomas, 60 mg of "TM-A59" from "TM-H59", 30 mg of "TM-A60" from "TM-H60", 30 mg of "TM-A65" from "TM-H65", 18 mg of "TM-A73" from "TM-H73", and 6 mg of "TM-A91" from "TM-H91". Those anti-TM monoclonal antibodies showed their corresponding properties described above.

EXAMPLE 3

Purification of TM by Immune Affinity Chromatography (1) Preparation of antibody column:

Cyanogen-bromide-activated Sepharose 4B (3 g) was washed successively with 1 mM hydrochloric acid and a 0.1M sodium carbonate buffer (pH 8.3) containing 0.1M of sodium chloride, and 8 ml of a solution of cyanogen-bromide-activated Sepharose 4B in the same buffer was obtained. Twenty milligrams of the monoclonal antibody TM-A59 obtained in Example 2 were added to the solution. The resultant mixture was shaken for 2 hours at room temperature and was then dewatered through a glass filter. Forty milliliters of a 1M tris-HCl buffer (pH 8.0) were added further, and the resultant mixture was shaken for 2 hours, followed by dewatering through a glass filter. Forty milliliters of a 0.1M acetate buffer (pH 4.0) were added, followed by dewatering through a glass filter. The thus-obtained antibody-conjugated Sepharose was washed three times alternately with a 0.1M HCl buffer (pH 8.3) containing 0.5M of sodium chloride and a 0.1 M acetate buffer (pH 4.0) containing 0.5M of sodium chloride, followed by equilibration with a 0.02M tris-HCl buffer (pH 7.6) containing 1M of sodium chloride and 0.05% of Lubrol PX to obtain an antibody column No. 59.

Similarly, antibody column Nos. 60 and 65 were obtained using "TM-A60" and "TM-A65" respectively.

(2) Purification of TM by the antibody columns:

Into each of the antibody columns prepared above, 500 $\mu$l of a solution containing 10 $\mu$g of TM extracted from human placenta was charged. The column was washed with 4 ml of the same buffer as that employed for its equilibration. The column was eluted with a 4 ml of 0.02M tris-HCl buffer (pH 7.6) which contained 1M of sodium chloride, 0.1% of Lubrol PX and 2M of potassium thiocyanate.

The amounts of TM recovered when the antibody column Nos. 59, 60 and 65 were used respectively were measured by the method to be described in Example 4. Results are summarized in Table 1.

TABLE 1

| Fraction | Monoclonal antibody | | |
|---|---|---|---|
| | No. 59 | No. 60 | No. 65 |
| Through | 0 | 0 | 11.4 |
| Washing | 5.0 | 5.6 | 15.6 |
| Eluate | 72.0 | 57.0 | 86.0 |

EXAMPLE 4

TM Assay Making Use of Anti-TM Monoclonal Antibody

Following the procedure reported by S. Yoshitake et al. [J. Biochem., 92, 1413–1424 (1982)], HRP was conjugated with the anti-TM monoclonal antibody. Using the resultant HRP-conjugated anti-TM monoclonal antibody, TM was measured by the ELISA method in the following manner.

Dissolved in a 0.05M sodium carbonate buffer was 40 $\mu$g/ml of a coating monoclonal antibody. The resultant solution was added in 100-$\mu$l portions into the individual wells of a 96-well microplate so as to coat the wells at 25° C. for 2 hours, then the wells were washed with a tris-HCl buffered saline containing 0.05% of "Tween 20" (trade name), the sample was dissolved in TBS-Tween which contained 5 mM of calcium chloride. The thus-prepared solution was added in 100-$\mu$l portion into the wells to conduct a reaction at 25° C. for 18 hours. Each well was then washed with TBS-Tween and then added with 100 $\mu$l of a diluted solution of the HRP-conjugated monoclonal antibody in TBS-Tween which contained 5 ml of calcium chloride, followed by a reaction at 25° C. for 4 hours. After washing each well with TBS-Tween, each well was added with 100 $\mu$l of a substrate solution (a 0.1M citrate-phosphate buffer containing 0.4 mg/ml of orthophenylenediamine and 0.01% of hydrogen peroxide; pH 5.0), followed by a further reaction at 25° C. for 60 minutes. Fifty microliters of 4.5M sulfuric acid were added to terminate the reaction and the absorbance at 492 nm was thereafter measured.

Figure 2:
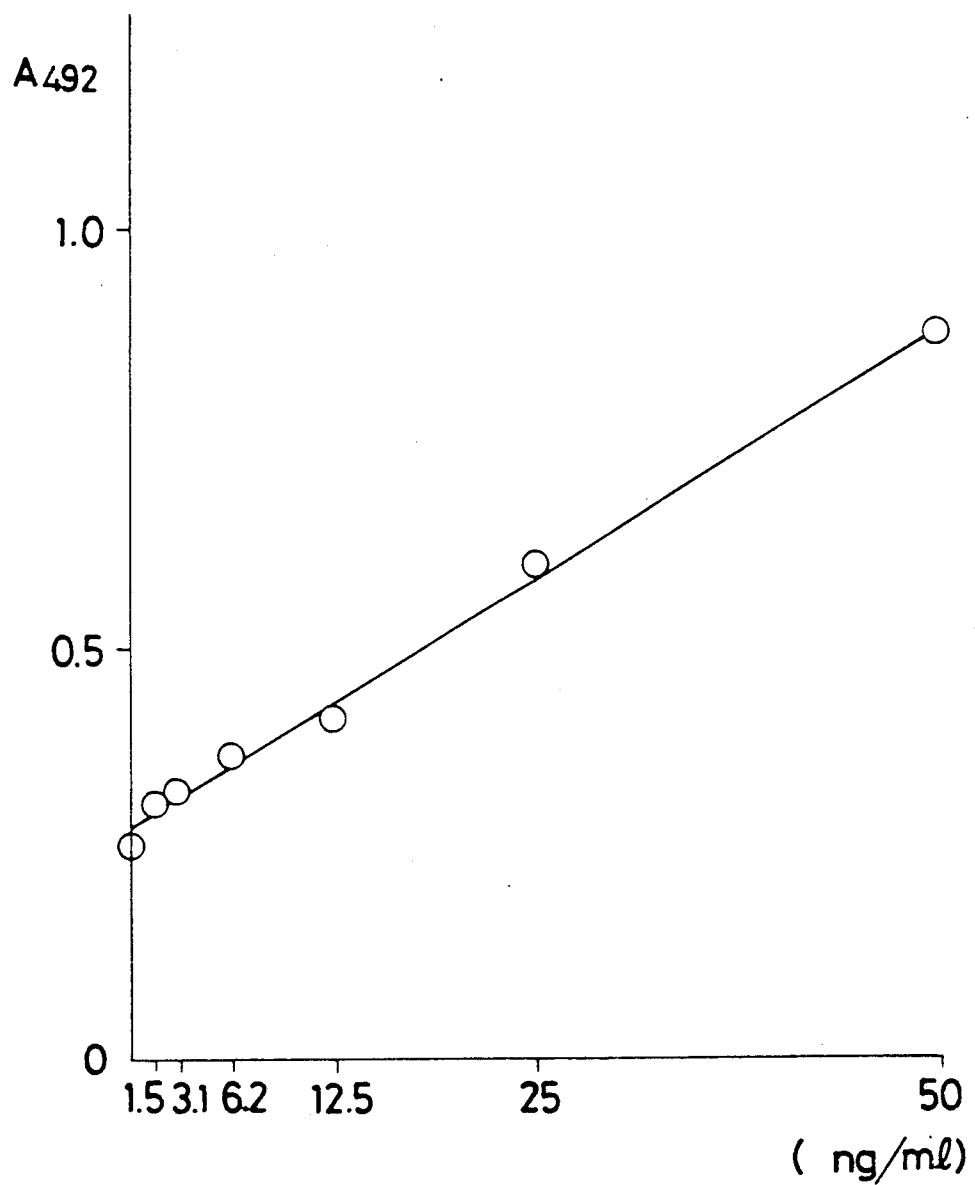
Figure 3:
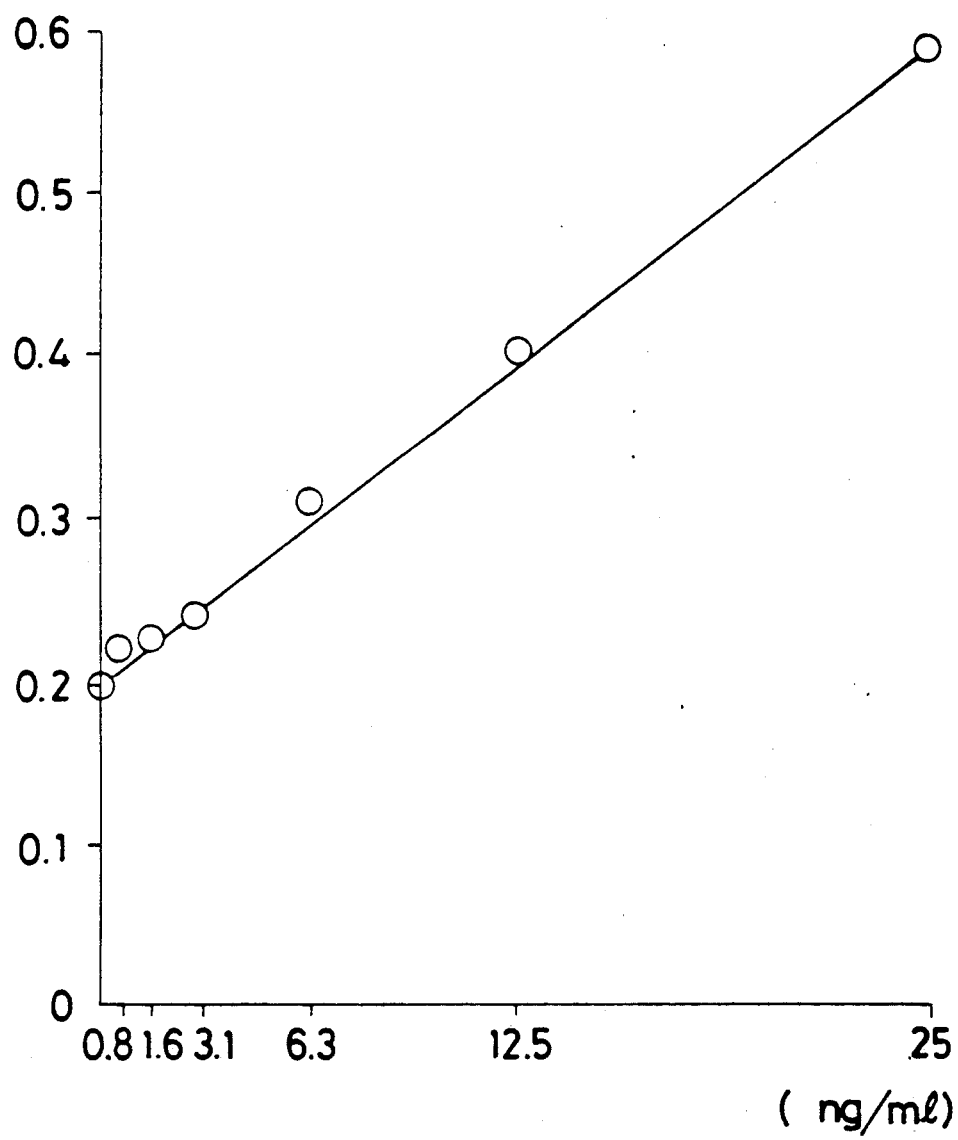
Figure 4:
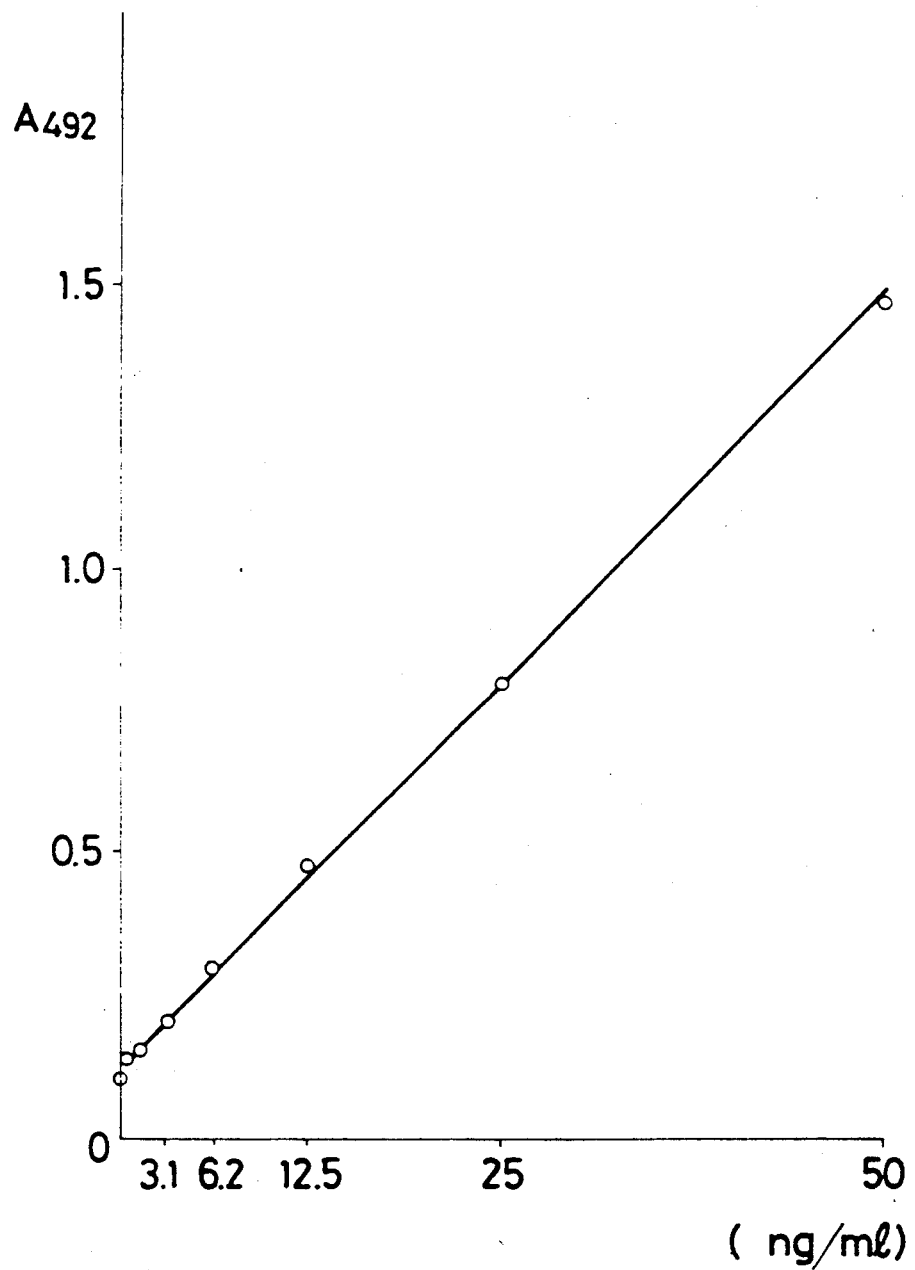

A calibration curve obtained when "TM-A59" and "TM-A73" were used respectively as a coating monoclonal antibody and a monoclonal antibody to be conjugated is shown in FIG. 1. A calibration curve obtained when "TM-A60" and "TM-A73" were used respectively as a coating monoclonal antibody and a monoclonal antibody to be conjugated is depicted in FIG. 2. A calibration curve obtained when "TM-A59" and "TM-A91" were used respectively as a coating monoclonal antibody and a monoclonal antibody to be conjugated is illustrated in FIG. 3. In addition, a calibration curve obtained when "TM-A59" and "TM-A60" were used respectively as a coating monoclonal antibody and a monoclonal antibody to be conjugated is shown in FIG. 4. They all had extremely high sensitivity and moreover exhibited good linearity. It is also understood that TM in a concentration range of 0.8–50 ng/ml is detectable.

Using serum samples of patients affected by disseminated intravascular coagulation (DIC) and those of healthy donors, their TM levels were measured by the above-described method. Whichever measurement system was employed, the serum samples of the DIC patients were found to contain TM as much as about 1.5 times compared with the serum samples of the healthy donors.

We claim:

1. A monoclonal antibody, TM-A60, produced from hybridoma TM-H60 deposited as FERM BP-1698, which is capable of specifically binding with human-derived thrombin-binding substance (TM), which binds thrombin and activates protein C, said monoclonal antibody having the following properties:
   (a) molecular weight: $180,000 \pm 8,000$.
   (b) IgG subclass: $IgG_1$.
   (c) isoelectric point: pH 7.9–9.2.
   (d) does not bind with the thrombin-binding site of the human-derived TM,
   (e) does not bind with the region where structural change is effected by calcium ions, and
   (f) does not bind with said human-derived TM digested with trypsin or elastase.

2. A hybridoma TM-H60, deposited as FERM BP-1698, which is obtained by fusing antibody-producing cells of an animal immunized with human-derived TM with myeloma cells, which hybridoma is capable of producing a monoclonal antibody specifically binding with said TM, and wherein said TM binds thrombin and activates protein C.

3. A process for purifying human-derived TM which binds thrombin and activates protein C, by immune affinity column chromatography, which comprises contacting said TM with monoclonal antibody TM-A60 produced from hybridoma TM-H60 deposited as FERM BP-1698 as an immunoadsorbent, thereby causing said monoclonal antibody to specifically bind with said TM.

4. An assay for TM, which comprises:
   a) contacting said TM with monoclonal antibody TM-A60 deposited as FERM BP-1698 which monoclonal antibody is capable of specifically binding with said TM; and
   b) detecting said TM.

* * * * *